United States Patent
Fang et al.

(10) Patent No.: US 9,724,005 B2
(45) Date of Patent: Aug. 8, 2017

(54) REAL-TIME MULTI-CHANNEL EEG SIGNAL PROCESSOR BASED ON ON-LINE RECURSIVE INDEPENDENT COMPONENT ANALYSIS

(71) Applicant: National Chiao Tung University, Hsinchu (TW)

(72) Inventors: Wai-Chi Fang, Hsinchu (TW); Wei-Yeh Shih, Hsinchu (TW); Jui-Chieh Liao, Hsinchu (TW); Kuan-Ju Huang, Hsinchu (TW); Chiu-Kuo Chen, Hsinchu (TW); Gert Cauwenberghs, Hsinchu (TW); Tzyy-Ping Jung, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 868 days.

(21) Appl. No.: 14/093,330

(22) Filed: Nov. 29, 2013

(65) Prior Publication Data
US 2014/0350864 A1    Nov. 27, 2014

(30) Foreign Application Priority Data
May 23, 2013   (TW) .............................. 102118193 U (51) Int. Cl.
| | |
|---|---|
| *A61B 5/0476* | (2006.01) |
| *G06F 17/16* | (2006.01) |
| *A61B 5/04* | (2006.01) |
| *G06F 17/18* | (2006.01) |
| *G06K 9/62* | (2006.01) |

(52) U.S. Cl.
CPC ........ *A61B 5/04012* (2013.01); *A61B 5/0476* (2013.01); *G06F 17/18* (2013.01); *G06K 9/624* (2013.01)

(58) Field of Classification Search
USPC ........................................................ 702/196
See application file for complete search history.

(56) References Cited

U.S. PATENT DOCUMENTS

2003/0046038 A1*   3/2003   Deligne ................. G06K 9/624
                                                                    702/190

* cited by examiner

*Primary Examiner* — Mohamed Charioui
(74) *Attorney, Agent, or Firm* — Mintz Levin Cohn Ferris Glovsky and Popeo, P.C.; Peter F. Corless; Steven M. Jensen (57) ABSTRACT

A real-time multi-channel EEG signal processor based on an on-line recursive independent component analysis is provided. A whitening unit generates covariance matrix by computing covariance according to a received sampling signal. A covariance matrix generates a whitening matrix by a computation of an inverse square root matrix calculation unit. An ORICA calculation unit computes the sampling signal and the whitening matrix to obtain a post-whitening sampling signal. The post-whitening sampling signal and an unmixing matrix implement an independent component analysis computation to obtain an independent component data. An ORICA training unit implements training of the unmixing matrix according to the independent component data to generate a new unmixing matrix. The ORICA calculation unit may use the new unmixing matrix to implement an independent component analysis computation. Hardware complexity and power consumption can be reduced by sharing registers and arithmetic calculation units.

8 Claims, 11 Drawing Sheets

REAL-TIME MULTI-CHANNEL EEG SIGNAL PROCESSOR BASED ON ON-LINE RECURSIVE INDEPENDENT COMPONENT ANALYSIS

TECHNICAL FIELD

The present invention relates to a technique of analyzing a brainwave independent component, and more particularly, to a real time multi-channel EEG signal processor based on an on-line recursive independent component analysis.

BACKGROUND

Neurons in brain operate constantly day after day. Electromagnetic waves (the so-called brainwaves) are transmitted among neurons. States of the brainwaves can be displayed through an electroencephalogram (EEG).

Specifically, an EEG is a diagram that records the potential difference of two points on a skull changing with time, usually in micro-volts. Generation of the potential difference relates to potential of the membrane. There are potential differences between both sides of the cell membrane. The extra negative ions in a cell attract positive ions outside the cell, and thus form the potential on the inner and outer layers of the cell membrane. The potential difference recorded by the EEG is collectively created by the thousands of neurons near the surface of the cerebral cortex, and is the consolidated potential of the majority of brain cells for a specific period of time, rather than the potential change of a single brain cell.

The potential change of neurons in brain recorded by measuring the brainwave may determine whether there is abnormal discharge or potential abnormal of the brain function, and can be used as a physician diagnosis, such as diagnosis of epilepsy, central nervous system or dementia psychosis. However, when measuring the brainwave, in order to pursue high spatial resolution to facilitate diagnosis, more measurement channels are used to improve the spatial resolution of the brainwave. An independent component analysis method is effective for separating independent component signal of the brainwave and the noise. However, in performing high channel independent analysis for the brainwave in the portable medical equipment, computation and complexity of the hardware are quite huge. It is a challenge for persons in the art to achieve an effective real time brainwave analysis, while taking into consideration the volume and hardware costs Therefore, there exists a need to achieve the real time analysis of the brainwave independent component by the hardware in a portable device.

SUMMARY

The present invention provides an effective VLSI hardware implementation to implement a multi-channel on-line recursive independent component analysis (ORICA) processor.

The present invention provides a real time multi-channel EEG signal processor based on on-line recursive independent component analysis (ORICA), including: an inverse square root matrix calculation unit for computation of eigen, eigen vector and inverse square root matrix; a whitening unit coupled to the inverse square root matrix calculation unit for covariance computation of a sampling signal to generate a covariance matrix, wherein the covariance matrix generates a whitening matrix based on the computation of the inverse square root matrix calculation unit; an ORICA calculation unit coupled to the inverse square root matrix calculation unit and the whitening unit for computing the sampling signal and the whitening matrix to obtain a post-whitening sampling signal, wherein an independent component analysis computation of the post-whitening sampling signal and a predetermined unmixing matrix is performed to obtain independent component data; and an ORICA training unit coupled to the inverse square root matrix calculation unit and the ORICA calculation unit for training the unmixing matrix according to the independent component data to obtain an inverse matrix of the unmixing matrix by the computation of the inverse square root matrix calculation unit, and computing the unmixing matrix and the inverse matrix of the unmixing matrix to generate a new unmixing matrix, wherein the new unmixing matrix is used for the ORICA calculation unit to perform a next independent component analysis computation of a next post-whitening sampling signal and the new unmixing matrix, so as to obtain next independent component data.

In one embodiment, the real time multi-channel EEG signal processor further includes a memory unit coupled to the inverse square root matrix calculation unit, the whitening unit, the ORICA calculation unit and the ORICA training unit for storing the sampling signal, the whitening matrix and the unmixing matrix.

In another embodiment, the ORICA training unit further comprises a nonlinearity module for computing the independent component data to obtain a non-linear transfer function; a kurtosis estimation module for identifying the independent component data to be a super Gaussian signal or sub-Gaussian signal and generating a kurtosis value; a multiplexer coupled to the nonlinearity module and the kurtosis estimation module for obtaining a nonlinear transfer function of the independent component distribution data in accordance with the Gaussian signal or the sub-Gaussian signal and the kurtosis value; a learning rate module for computing a learning rate determining convergence and steady state performance of the unmixing matrix during training; and a weight training module for implementing an iterative computation using the independent component data, the nonlinear transfer function of the independent component distribution data, the learning rate and the unmixing matrix, so as to generate the next unmixing matrix.

Also, the whitening unit of the real time multi-channel EEG signal processor contains an average covariance module having a multiply-adder.

In addition, the ORICA training unit of the real time multi-channel EEG signal processor further includes a learning rate module coupled to the weight training module for providing a plurality of learning rates, so as for the ORICA training unit to change a convergence rate of the unmixing matrix.

Furthermore, the inverse square root matrix calculation unit of the real time multi-channel EEG signal processor contains a singular value decomposition processor, a floating point square root module and a floating point divider.

Compared to the prior art, the real time multi-channel EEG signal processor based on on-line recursive independent component analysis has four arithmetic units and a shared memory unit. With the design of sharing the memory and sorting the data flow, each one of the arithmetic units uses the memory unit in order, so as to achieve smaller memory complexity and lower power consumption. Accordingly, the present invention effectively implements the multichannel ORICA processor with VLSI hardware for performing independent component analysis of the brainwave, such that separation of the brainwave signal and noise is subsequently implemented. Therefore, real time, light and portable implementing separation and monitor of the brainwave signal and noise can be achieved, and can be used as applications on a fast, lightweight and portable medical equipment.

BRIEF DESCRIPTION OF THE DRAWINGS

The present disclosure can be more fully understood by reading the following detailed description of the preferred embodiments, with reference made to the accompanying drawings, wherein.

DETAILED DESCRIPTION OF THE EMBODIMENTS

The present disclosure is described by the following specific embodiments. Those with ordinary skills in the arts can readily understand the other advantages and functions of the present disclosure after reading this specification.

Figure 1:
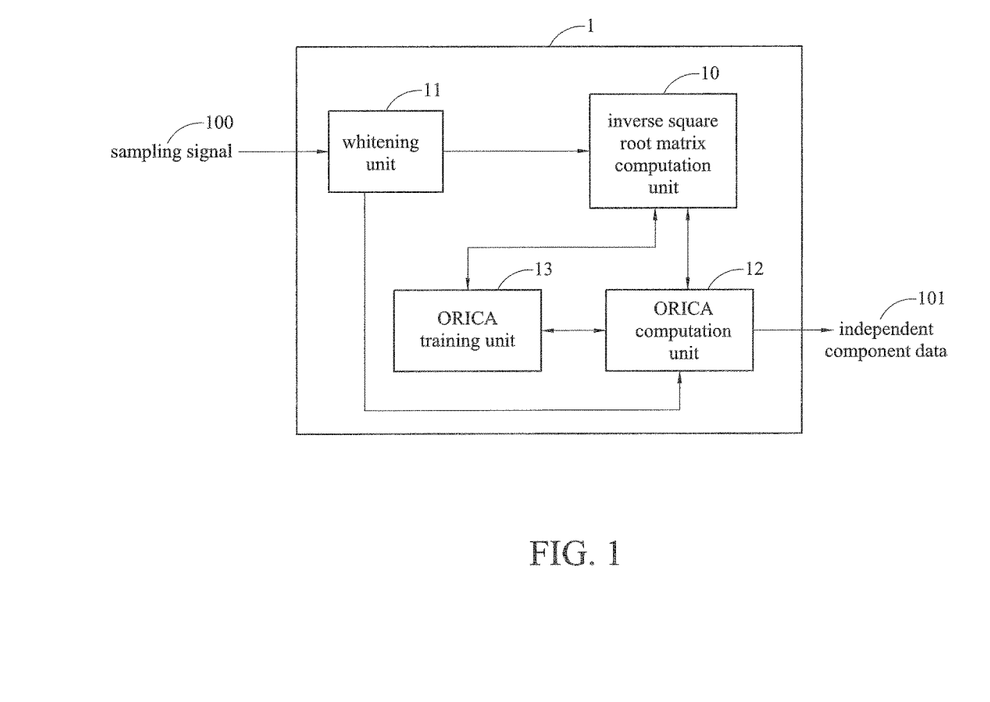
FIG. 1 is a block schematic diagram depicting a real time multi-channel EEG signal processor based on an on-line recursive independent component analysis in accordance with the present disclosure.

Referring to FIG. 1, FIG. 1 is a block schematic diagram depicting a real time multi-channel EEG signal processor based on an on-line recursive independent component analysis in accordance with the present disclosure As shown in FIG. 1, the real time multi-channel EEG signal processor 1 based on on-line recursive independent component analysis includes a inverse square root matrix calculation unit 10, a whitening unit 11, an ORICA calculation unit 12, and an ORICA training unit 13.

The inverse square root matrix calculation unit 10 is used for a computation of eigen, eigen vector and inverse square root matrix. Specifically, the inverse square root matrix calculation unit 10 mainly executes and provides matrix computation of data such as eigen, eigen vector or inverse square root matrix, for the ORICA calculation unit or the ORICA training unit.

The whitening unit 11 is coupled to the inverse square root matrix calculation unit 10. The whitening unit 11 may be used for covariance computation of the received sampling signal 100 to generate a covariance matrix. The covariance matrix will be sent to the inverse square root matrix calculation unit 10 for computation in order to obtain a whitening matrix.

The ORICA calculation unit 12 is coupled to the inverse square root matrix calculation unit 10 and the whitening unit 11, and is used for computation of the sampling signal 100 and the whitening matrix generated by the whitening unit 11, so as to whiten the sampling signal 100 to obtain a post-whitening sampling signal. The whitening process described herein is to remove data dependencies between data of the sampling signal 100. Since the ORICA computation needs iterative training to compute the convergent unmixing matrix, pre-whitening can accelerate the above process.

In addition, the ORICA calculation unit 12 is also used for implementing independent component analysis computation of the post-whitening sampling signal and a predetermined unmixing matrix, in order to obtain independent component data 101. This ORICA computation is to analyze the independent component analysis within the sampling signal and distinguish useful signals from noise signals of the brainwave signals. Therefore, the ORICA calculation unit 12 implements computation of the independent component analysis of the post-whitening sampling signal and unmixing matrix, and the independent component data 101 are thus obtained.

The ORICA training unit 13 is coupled to the inverse square root matrix calculation unit 10 and the ORICA calculation unit 12. The ORICA training unit 13 implements training of the original unmixing matrix, according to the independent component data generated by the ORICA calculation unit 12. The training means that the inverse matrix of the unmixing matrix is obtained via the inverse square root matrix calculation unit 10, and the computation of the unmixing matrix and the inverse matrix of the unmixing matrix are implemented to generate a new unmixing matrix. The new unmixing matrix is used for the ORICA calculation unit 12 to implement computation of the independent component analysis of the next post-whitening sampling signal and the new unmixing matrix in the next computation process of the independent component analysis, so as to obtain the new independent component data 101. The training performed by the ORICA training unit 13 requires iterative training to achieve convergence and obtain the more accurate unmixing weight matrix, in that the ORICA computation has an adaptive learning rule.

From the above, in the computation process of the independent component data 101, the ORICA calculation unit 12 implements independent component analysis of the post-whitening sampling signal and the unmixing matrix, that is, each post-whitening sampling signal is implemented by a computation with the trained unmixing matrix, so as to generate the independent component data 101.

It should be noted, due to the computation characteristic of the ORICA, for sampling rate of 128, the computation output of the ORICA must be implemented prior to sampling completion of the next data, within $1/128$ seconds. That is, in limit under time specifications of the real-time computation, the designed ORICA processor uses mixed parallel architecture, that is different hardware parallelism is allocated in accordance with the computing complexity of the processing unit. Thus, to avoid the time- and energy-consuming computation, in addition to performing the ORICA computation, the real time multi-channel EEG signal processor based on on-line recursive independent component analysis of the present invention uses a shared buffer and shared arithmetic computation.

Accordingly, in another embodiment, the real time multi-channel EEG signal processor based on on-line recursive independent component analysis of the present invention further includes a memory unit for storing data such as the sampling signal 100, the whitening matrix and the unmixing matrix. The memory unit is coupled to the inverse square root matrix calculation unit 10, the whitening unit 11, the ORICA calculation unit 12 and the ORICA training unit 13, for temporarily storing data generated by the inverse square root matrix calculation unit 10, the whitening unit 11, the ORICA calculation unit 12 and the ORICA training unit 13, in order to achieve effective data arrangements and memory sharing.

In order to clearly illustrate the internal architecture of the real time multi-channel EEG signal processor based on on-line recursive independent component analysis of the present invention, FIGS. 2 and 3A-3D further illustrate the internal structure of the real time multi-channel EEG signal processor based on on-line recursive independent component analysis.

Figure 2:
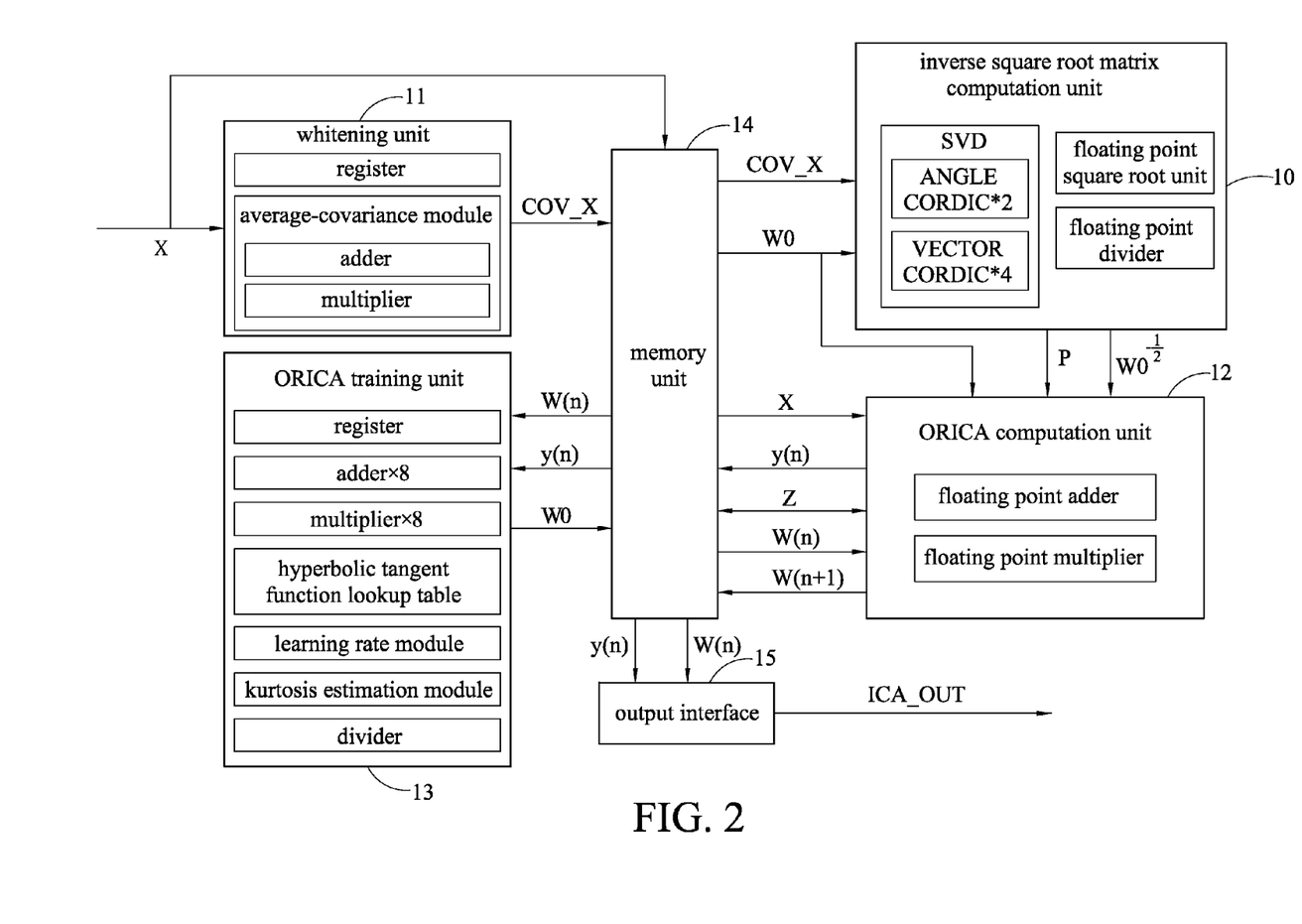
FIG. 2 is a schematic diagram depicting the real time multi-channel EEG signal processor based on the on-line recursive independent component analysis in accordance with an embodiment of the present disclosure.

FIG. 2 is a schematic diagram depicting the real time multi-channel EEG signal processor based on the on-line recursive independent component analysis in accordance with an embodiment of the present disclosure. As shown in FIG. 2, the real time multi-channel EEG signal processor 1 based on on-line recursive independent component analysis includes the inverse square root matrix calculation unit 10, the whitening unit 11, the ORICA calculation unit 12, the ORICA training unit 13, the memory unit 14, and the output interface 15.

The inverse square root matrix calculation unit 10 has a singular value decomposition (SVD) processor, a floating point square root unit and a floating point divider, wherein the singular value decomposition processor includes two angle coordinate rotation digital computers and four vector coordinate rotation digital computers.

The whitening unit 11 mainly has a register, an average-covariance module and an adder and a multiplier located in the average-covariance module.

The ORICA calculation unit 12 includes a floating point adder and a floating point multiplier.

The ORICA training unit 13 is formed by a register, eight adders, eight multipliers, a divider, a hyperbolic tangent function lookup table, a learning rate module and a kurtosis estimation module.

In order to achieve the shared memory, the memory unit 14 can be coupled to the inverse square root matrix calculation unit 10, the whitening unit 11, the ORICA calculation unit 12, the ORICA training unit 13 and the output interface 15, for storing or temporarily storing needed or generated data of each unit.

The output interface 15 may output the independent component data and the former trained unmixing matrix. The output result, ICA_OUT, is an element of the independent component data y(n) and the unmixing matrix W(n) to serially output column by column.

Based on the internal structure and relationship of the foregoing units, data transmission states between the units will be specifically described as follows.

The whitening unit 11 obtains the sampling signal X from the outside, and the sampling signal X can be sent to the memory unit 14 for storage. The whitening unit 11 implements the covariance computation through the ORICA calculation unit 12 for generating the covariance matrix COV_X. The covariance matrix COV_X is transmitted to the inverse square root matrix calculation unit 10 for implementing computation in order to obtain a whitening matrix P.

The ORICA calculation unit 12 can obtain the original sampling signal X which is not whitened from the memory unit 14 to be implemented by a computation with the whitening matrix P, so as to whiten the sampling signal X. Afterwards, the post-whitening sampling signal Z can be obtained and sent back to the storage unit 14 for temporary storage.

The ORICA training unit 13 obtains the post-whitening sampling signal Z and the unmixing matrix W(n) from the memory unit 14 and implements the independent component analysis computation of the post-whitening sampling signal Z and the unmixing matrix W(n) through the ORICA calculation unit 12, in order to obtain independent component data y(n), and stores it in the memory unit 14.

In addition, the ORICA training unit 13 implements training of the original unmixing matrix W(n) according to the independent component data y(n) generated by the ORICA calculation unit 12, to compute the unmixing matrix W0 which is not whitened. The training includes the computation by the inverse square root matrix calculation unit 10 to obtain the inverse matrix $W0^{-1/2}$ of the un-whitening unmixing matrix W0. The ORICA training unit 13 implements computation of the un-whitening unmixing matrix W0 and the inverse matrix $W0^{-1/2}$ of the un-whitening unmixing matrix through the ORICA calculation unit 12, to generate a new unmixing matrix W(n+1). The new unmixing matrix W(n+1) generated by the training provides the ORICA calculation unit 12 with replacing the original unmixing matrix W(n) in the next independent component analysis computation. The independent component analysis computation of the next post-whitening sampling signal Z and the new unmixing matrix W(n+1) is implemented, such that a new independent component data y(n+1) will be obtained. The generated new unmixing matrix W(n+1) and the new independent component data y(n+1) are temporarily stored in the memory unit 14.

The output interface 15 may output the independent component data y(n) (followed by y(n+1), . . . ) and the unmixing matrix W(n) (followed by W(n+1), . . . ).

From the foregoing, the data of the inverse square root matrix calculation unit 10, the whitening unit 11, the ORICA calculation unit 12 and the ORICA training unit 13 may be stored in the memory unit 14. In addition, the ORICA calculation unit 12 implements computations from the whitening unit 11 and the ORICA training unit 13. Through the effective data arrangement, each calculation unit using the memory is ordered. The demand for memory is significantly reduced so as to achieve effective memory sharing, while the design of a smaller memory complexity and low power consumption can be achieved.

FIGS. 3A to 3D are schematic diagrams depicting internal operation of each unit of the real time multi-channel EEG signal processor based on the on-line recursive independent component analysis in accordance with the present disclosure.

Figure 3A:
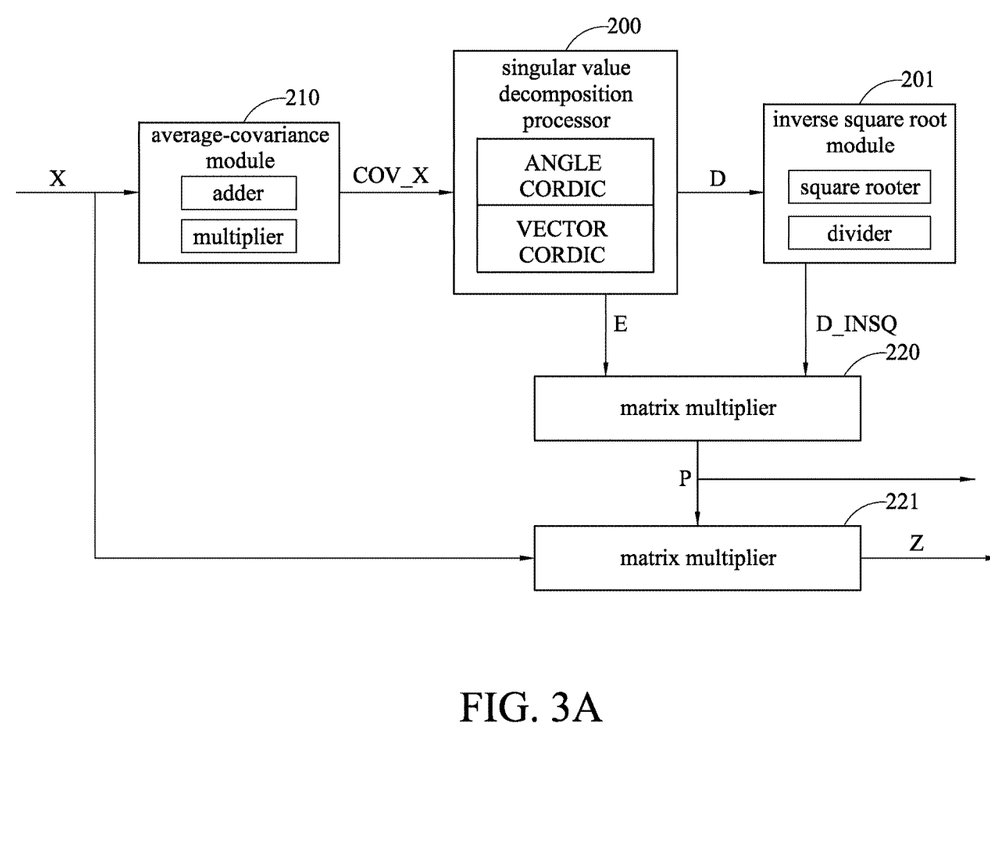
FIGS. 3A to 3D are schematic diagrams depicting internal operation of each unit of the real time multi-channel EEG signal processor based on the on-line recursive independent component analysis in accordance with the present disclosure.

As shown in FIG. 3A, steps of the whitening process is described. The sampling signal X is obtained and transmitted to the average-covariance module 210 for generating a covariance matrix COV_X. The covariance matrix COV_X is transmitted to the singular value decomposition processor 200 in the inverse square root matrix calculation unit 10 of FIG. 2. The singular value decomposition processor 200 includes the angle coordinate rotation digital computer and the vector coordinate rotation digital computer. Upon processing of the singular value decomposition processor 200, the covariance matrix COV_X obtains diagonal matrix D and orthogonal matrix E. The diagonal matrix D and the orthogonal matrix E contain a covariance matrix eigen and a covariance matrix eigen vector.

The diagonal matrix D generates the inverse matrix D_INSQ of the diagonal matrix D through computation of the inverse square root module 201. The matrix multiplier 220 in the ORICA calculation unit 12 of FIG. 2 is used for computing the orthogonal matrix E and the inverse matrix D_INSQ of the diagonal matrix D, to generate a whitening matrix P. In addition, the matrix multiplier 221 is used for computing the sampling signal X and the whitening matrix P, in order to obtain the post-whitening sampling signal Z.

Figure 3B:
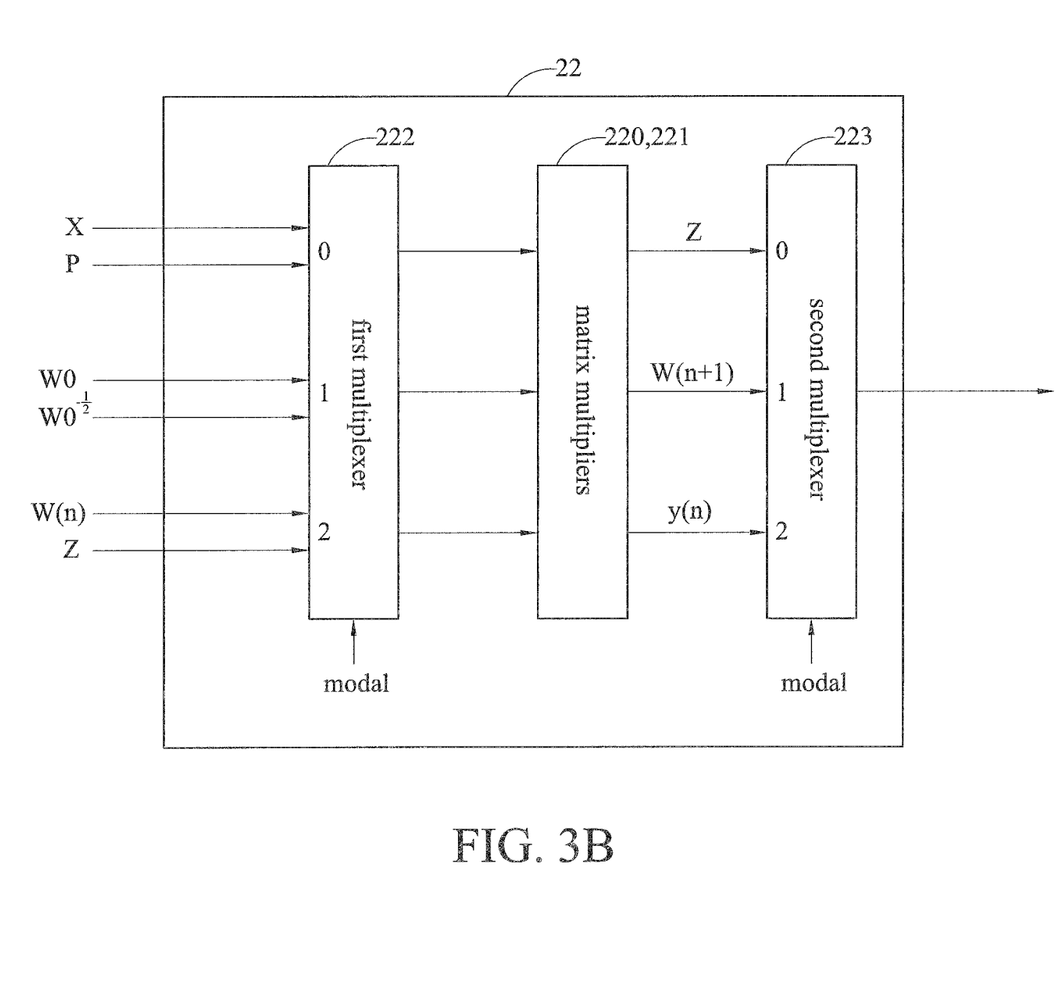

As shown in FIG. 3B, the computing process provided in the ORICA calculation unit 22 is described. The ORICA calculation unit 22 provides the independent component analysis and outputs the result. The ORICA calculation unit 22 implements individual computations of the sampling signal X and the whitening matrix P, the unmixing matrix W0 and the inverse matrix $W0^{-1/2}$, and the unmixing matrix W(n) and the post-whitening sampling signal Z, respectively. The data are respectively sent to the first multiplexer 222. Based on the control of the mode of the first multiplexer 222, which input should be implemented by computation is determined and sent to the matrix multipliers 220 and 221. The respective computing results, such as the post-whitening sampling signal Z generated by computing the sampling signal X and the whitening matrix P, the new unmixing matrix W(n+1) generated by computing the unmixing matrix W0 and the inverse matrix $W0^{-1/2}$, and the independent component data y(n) generated by computing the unmixing matrix W(n) and the post-whitening sampling signal Z, are obtained, and the mode of the second multiplexer 223 is selectively controlled to input associated data. For example, the unmixing matrix W is trained to change the value, and therefore through the computing of the matrix multipliers 220 and 221, the n-th unmixing matrix W(n) and the post-whitening sampling signal Z generate the n-th independent component data y(n), so that the independent component analysis will be completed. Further, in order to achieve sharing of hardware, the matrix multiplier selects the input for computation based on different mode demands.

Figure 3C:
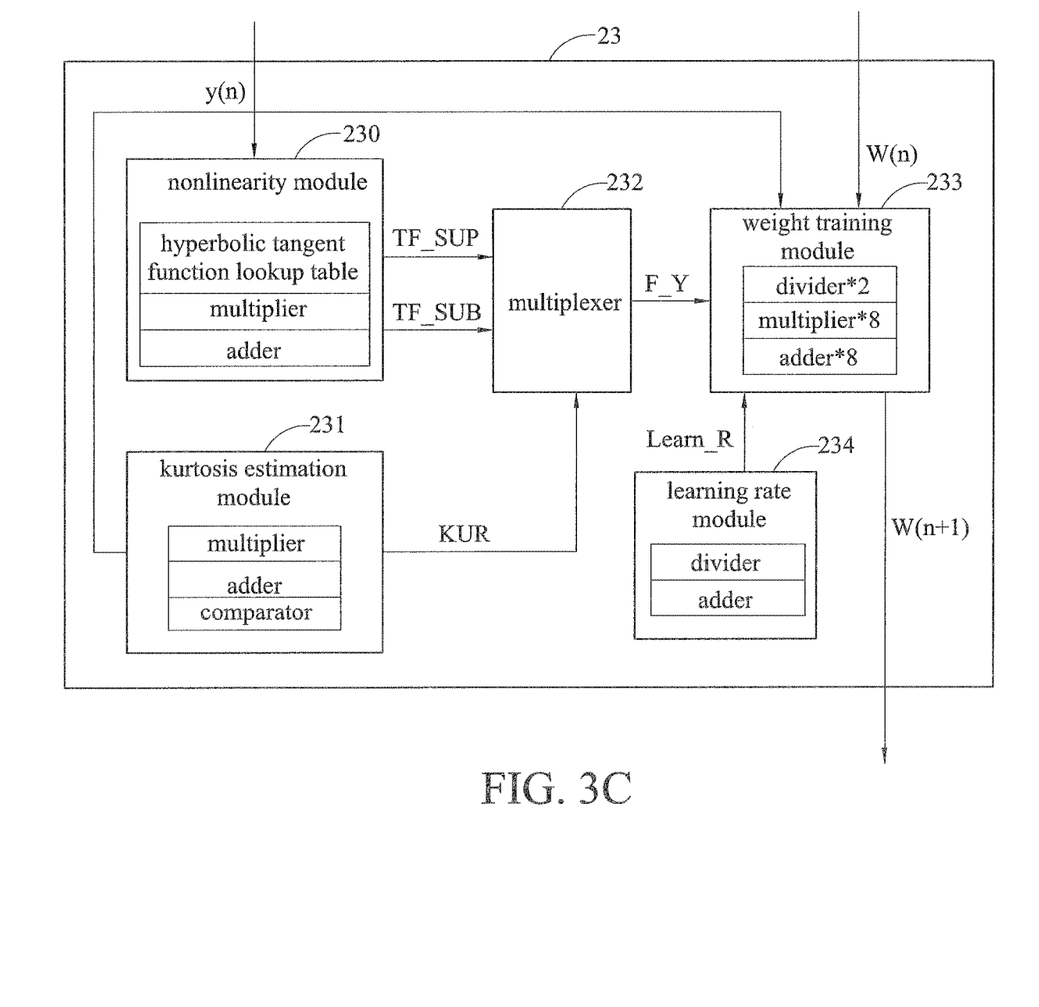

Subsequently, as shown in FIG. 3C, the operations within the ORICA training unit 23 are described. The ORICA training unit 23 has a nonlinearity module 230, a kurtosis estimation module 231, a multiplexer 232, a weight training module 233 and a learning rate module 234.

The ORICA training unit 23 transmits the n-th independent component data y(n) to the nonlinearity module 230, the kurtosis estimation module 231 and the weight training module 233. The nonlinearity module 230 is used for distribution of the n-th independent component data y(n) to obtain the non-linear transfer function. The kurtosis estimation module 231 is used for identifying the independent component data as a super Gaussian signal or a sub-Gaussian signal and generating a kurtosis value KUR sent to the multiplexer 232. The multiplexer 232 receives the kurtosis value KUR, the value TF_SUP (the value is 1) representing the super Gaussian distribution from the nonlinearity module 230 and the value TF_SUB (the value is 0) representing the sub-Gaussian distribution from the nonlinearity module 230, to generate the nonlinear transfer function of the independent component distribution data and obtain the nonlinearity F_Y.

The weight training module 233 is the most important part of the ORICA training unit 23, and is used for computing the (n+1)-th unmixing matrix W(n+1), that is, implementing iterative computation using the nonlinear conversion function of the independent component data y(n), the independent component distribution data, the learning rate LEARN_R and the unmixing matrix, so as to generate a new unmixing matrix.

In addition, the aforementioned learning rate LEARN_R means that prior to computing the (n+1)-th unmixing matrix W(n+1), the learning rate module 234 determines the learning rate LEARN_R. The learning rate module 234 is an automatic learning program. At the beginning, the learning rate LEARN_R is a greater value, and is gradually decreased for converging the ORICA training unit 23. Therefore, upon the nonlinearity F_Y, the learning rate LEARN_R and the n-th unmixing matrix W(n) are determined, the weight training module 233 computes the (n+1)-th unmixing matrix W(n+1) and transmits the result to the memory unit for a next independent component analysis computation.

Figure 3D:
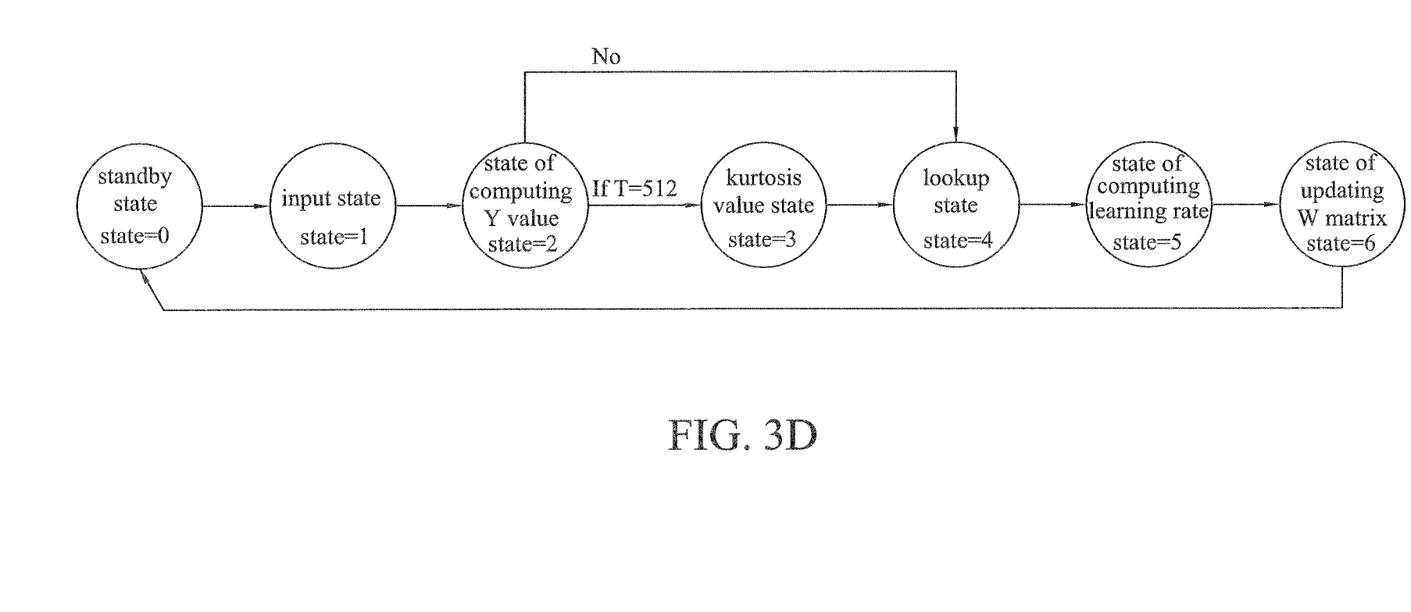

As shown in FIG. 3D, the operation of the ORICA training unit 23 of FIG. 3C is illustrated based on the mathematical model of the finite state machine.

At the beginning, the state machine is placed in standby state (state=0). When the post-whitening brainwave (EEG), the post-whitening sampling signal Z, is input, the state machine is entered to input state (state=1), and the input signal is stored in the register. After the input, the state machine is entered to state of computing Y value (independent component data) (state=2). The unmixing matrix W is called from the memory unit. The post-whitening sampling signal Z is computed by the vector multiply-adder. The kurtosis value computation needs 512 Y values, in order to achieve the real-time computation. Each calculated Y value will be implemented by computations of square and the power of four, respectively, and added with the prior accumulation stored in multiple registers, and then stored in those registers. That is, when the kurtosis value counter is equal to 512, the 512 data are accumulated, and the state machine is entered to the kurtosis value state (state=3). After computing, the kurtosis value equal to 1 is the super Gaussian channel, and the kurtosis value equal to 0 is the sub-Gaussian channel.

The kurtosis value counter will reset to zero for next computing. When the kurtosis value counter is less than 512, the state machine is directly entered to lookup state (state=4). The further computation is implemented based on the kurtosis value, which is the difference of the super Gaussian and sub-Gaussian. Afterwards the state machine is entered to state of computing the learning rate (state=5). The learning rate determines the calculated accuracy and convergence rate of the training module. In other words, the learning rate affects the convergence rate and the accuracy.

Once the learning rate is determined, the state machine is entered to state of updating the W matrix (state=6), that is, the calculated new unmixing matrix W is output to the memory unit. The state machine will once again be entered to the standby state state=0, for the next input.

Figure 4:
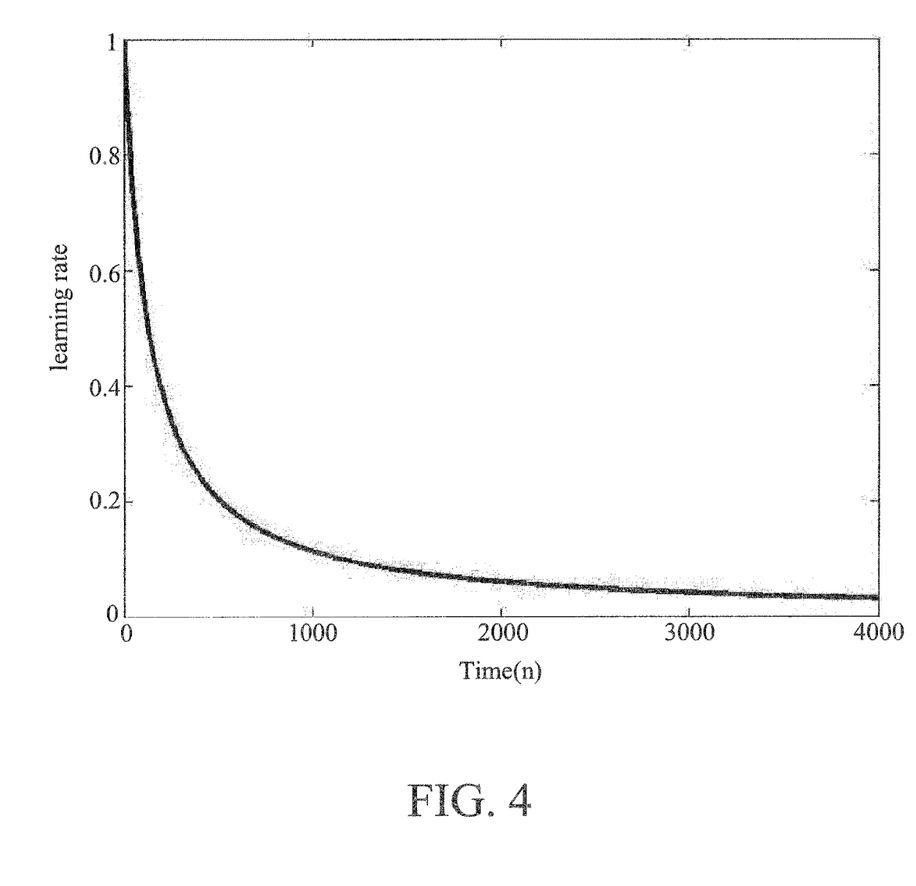
FIG. 4 is a diagram showing relationship between the learning rate and time in the real time multi-channel EEG signal processor based on the on-line recursive independent component analysis in accordance with the present disclosure.

Referring to FIG. 4, FIG. 4 is a diagram showing relationship between learning rate and time in the real time multi-channel EEG signal processor based on the on-line recursive independent component analysis in accordance with the present disclosure. As shown in FIG. 4, the learning rate will affect the accuracy and the convergence rate calculated by the weight training module. If the learning rate is too large, although the convergence rate is fast, the accuracy is poor. If the learning rate is too small, the convergence rate is slower and the accuracy is better. The simulation is implemented using Matlab, and the curve shown in FIG. 4 is formed. At the beginning, the learning rate is larger. With converging the data and increasing the times of training, the learning rate is decreased gradually, so as to achieve the fast convergence and good computing accuracy.

Figure 5A:
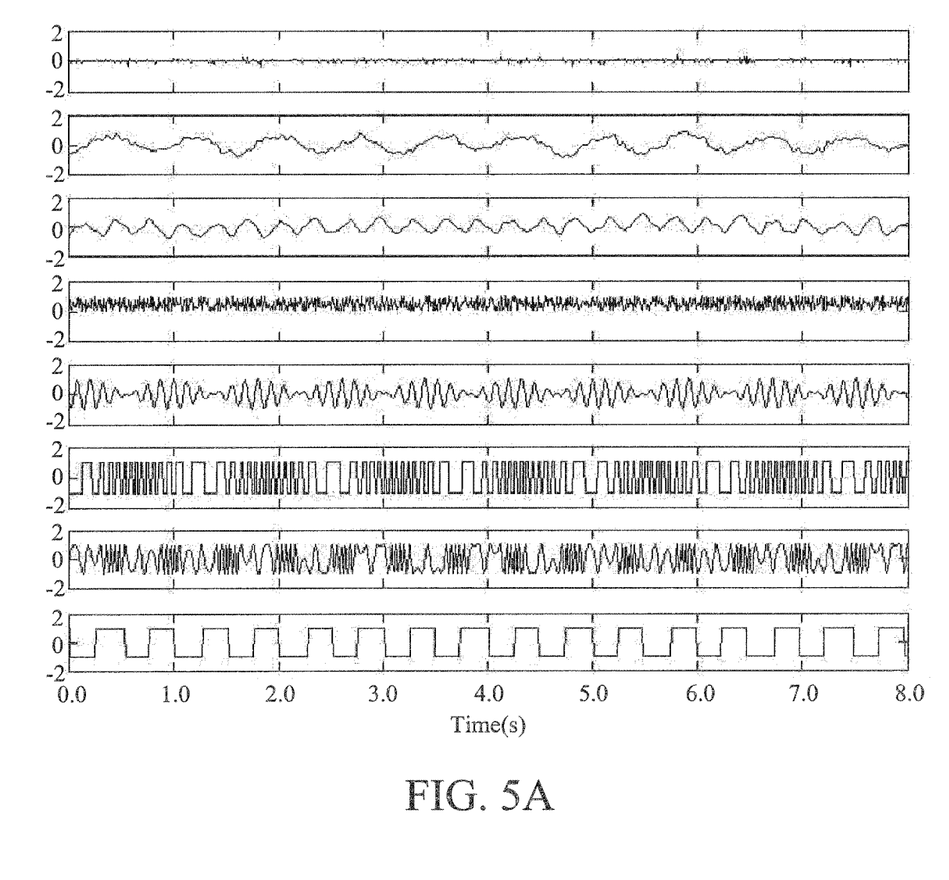
FIGS. 5A to 5C are signal diagrams showing simulation of the real time multi-channel EEG signal processor based on the on-line recursive independent component analysis in accordance with the present disclosure.
Figure 5B:
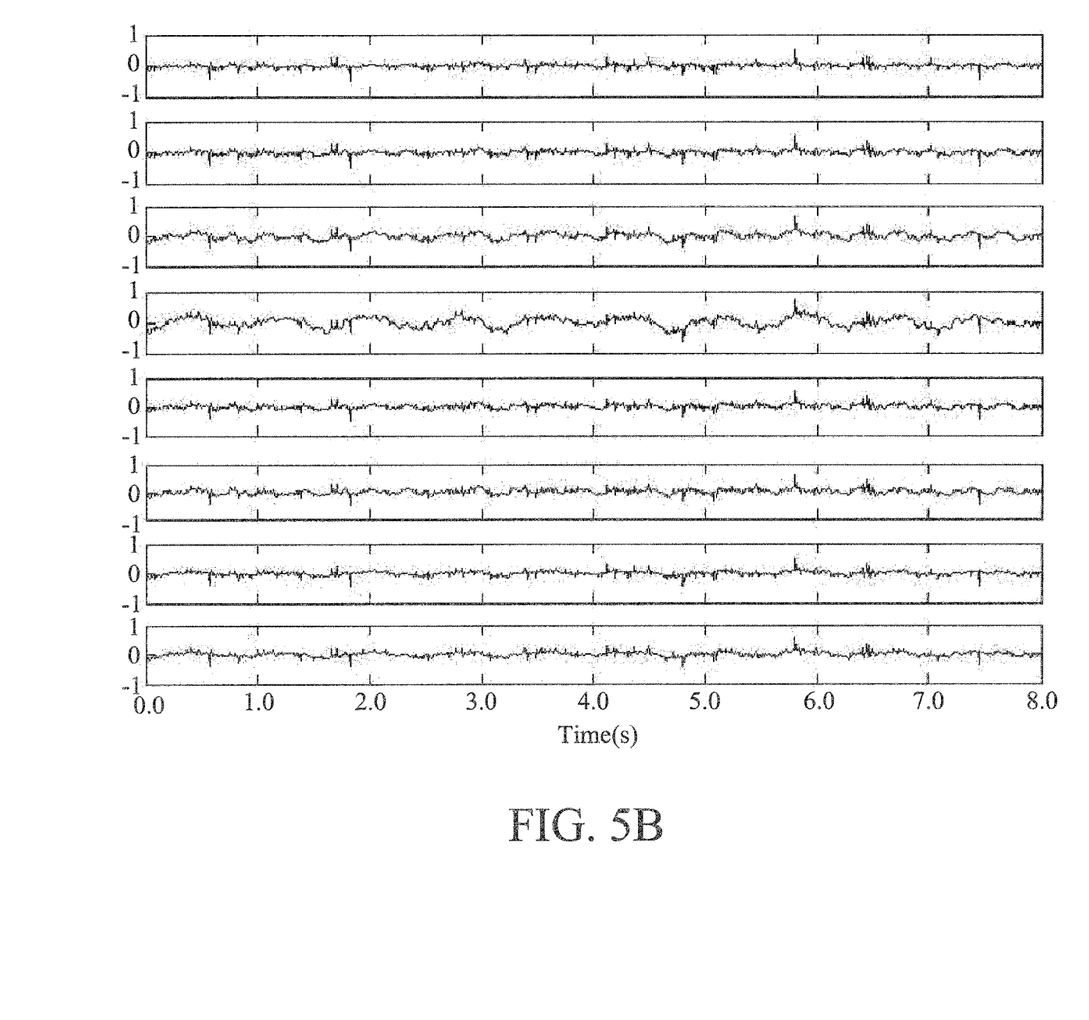
Figure 5C:
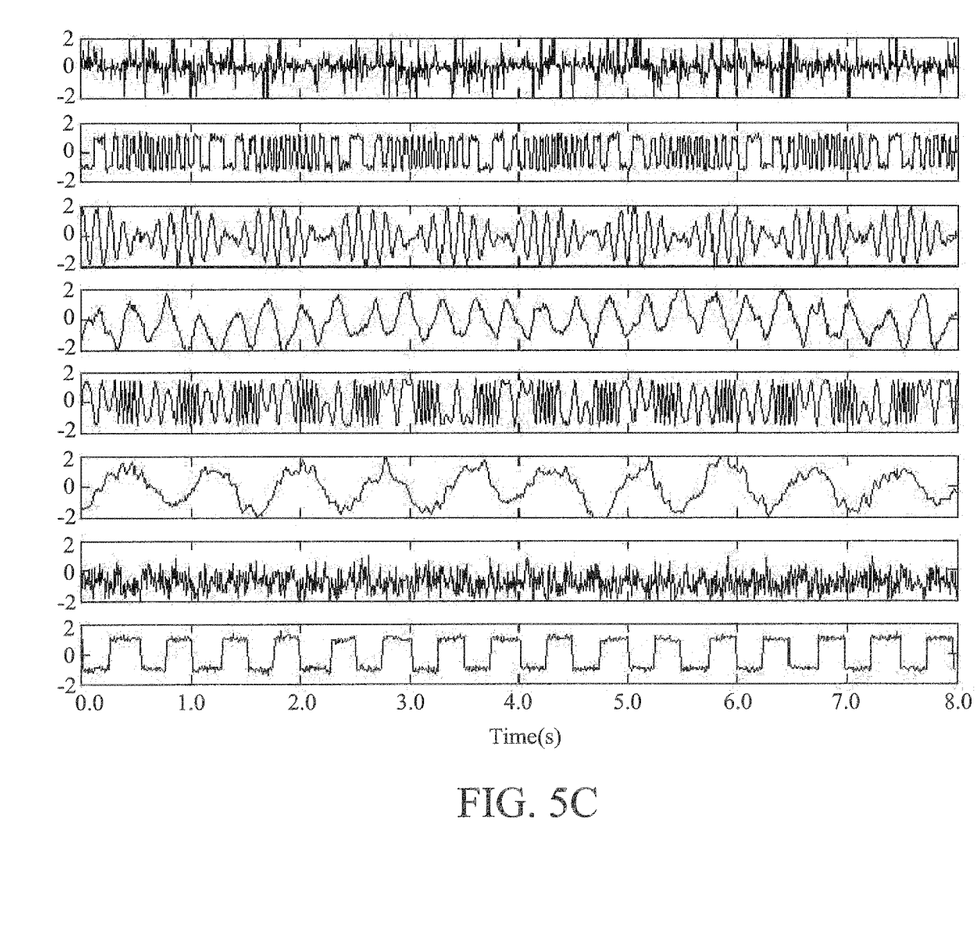

FIGS. 5A to 5C are diagrams showing simulation of the real time multi-channel EEG signal processor based on the on-line recursive independent component analysis in accordance with the present disclosure. The forementioned figures take the 8-channel EEG formula based processor for example, and simulation results of the brainwave signal and the super Gaussian and the sub-Gaussian test signal are entered. As shown in FIG. 5A, distribution of the original source signals of each channel is shown, i.e., the independent source signals simulating the super Gaussian and the sub-Gaussian the generated by the Matlab. The tested mixed signal is further generated with multiplying the random matrix and the source signal, as the distribution of the mixed signal of each of the channels as shown in FIG. 5B. The tested mixed signal is input to the real time multi-channel EEG signal processor based on on-line recursive independent component analysis of the present invention to generate the output result, and the distribution of the extracted ORICA signal of each channel is generated as shown in FIG. 5C. Afterwards correlation comparison between the independent source signal (FIG. 5A) and the output results is performed. The result of the real time multi-channel EEG signal processor based on on-line recursive independent component analysis of the present invention under the simulation test is consistent with the result under the off-line mode, and will not be affected by the present invention implementing independent component analysis using the real-time computing process.

Figure 6:
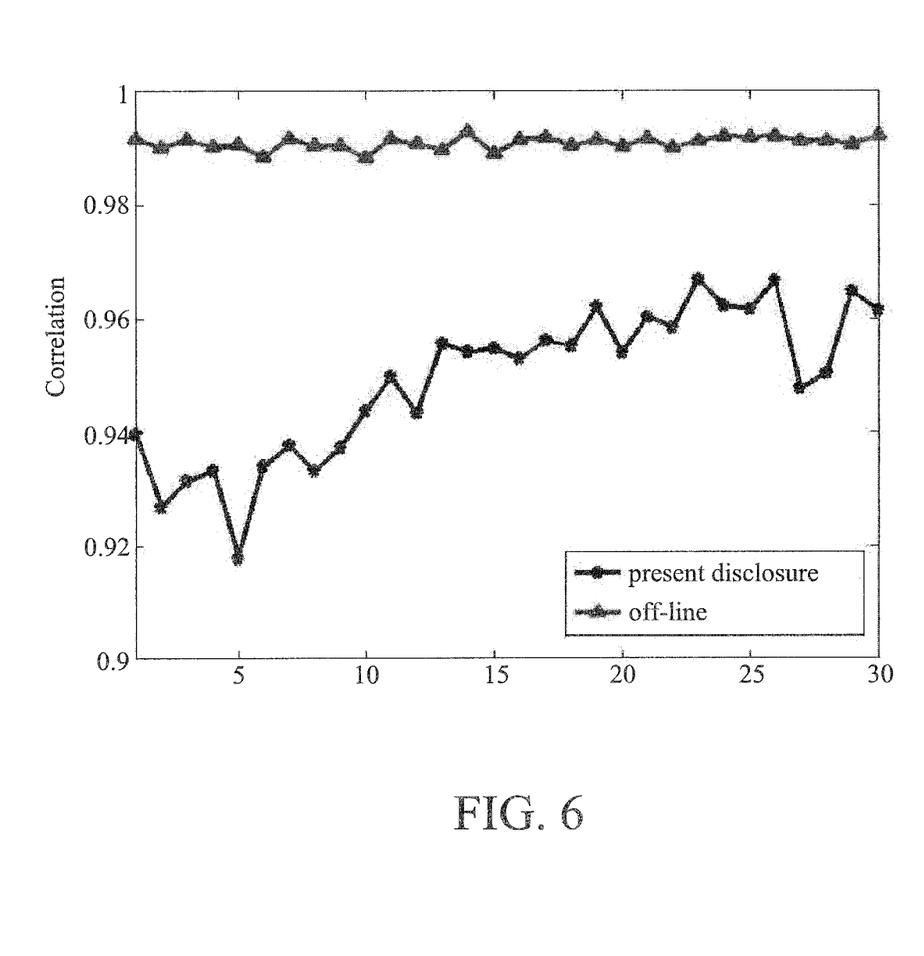
FIG. 6 is a diagram showing results and off-line processing of the real time multi-channel EEG signal processor based on the on-line recursive independent component analysis in accordance with the present disclosure.

FIG. 6 is a diagram showing results and off-line processing of the real time multi-channel EEG signal processor based on the on-line recursive independent component analysis in accordance with the present disclosure. FIG. 6 shows that the correlation of the sampling signal of the original source and the extracted ICA signal is compared to show the difference of the effect of the brainwave signal processing between on-line implementation and off-line implementation. As shown in FIG. 6, in general, the result correlation of the off-line is better than the correlation of the result of the on-line processing. However, in analyzing the correlation of the original sampling signal and the extracted ICA signal, the average correlation coefficient of the real time multi-channel EEG signal processor of the present invention is 0.9583 per second signal frame, which is similar to the difference in the correlation between the two under the off-line mode. That is, through the real time multi-channel EEG signal processor based on on-line recursive independent component analysis of the present invention, in the real time multi-channel, the result is not poorer than the processing of the off-line mode.

In a particular embodiment, according to the volume size, cost considerations and objects, etc., the real time multi-channel EEG signal processor based on on-line recursive independent component analysis of the present invention may be designed and manufactured by the following data. For example, chip area is 800×800 um$^2$, operating frequency is up to 50 MHz. The power of the chip is implemented as simulation power with Nanosim. The power is about 4.18 mW at 1.0V, under operating frequency of 50 MHz. The chip can be used in portable EEG measurement equipment, so as to achieve small size and be easily portable.

The present invention allocates the hardware computing the complexity based on the computed timing and the complexity. Under the limitations of the real-time timing specification, the high computing complexity is given a higher parallelism, and the low computing complexity employs order. In addition, the design of fixed point and floating point is used when computing. Bandwidth of data is assessed and simulated in order to design a data width with an appropriate fixed point. Data required high accuracy further uses floating point data width and uses hardware sharing to save hardware costs and power consumption. The present invention utilizes various design features in multi-channel real-time specification, to achieve effective design of hardware processing unit and low input memory hardware complexity, and the power consumption is reduced.

In summary, the real time multi-channel EEG signal processor based on on-line recursive independent component analysis of the present invention achieves effective data arrangement through the design of sharing memory and sorting data flow, such that each calculation unit uses memory unit in order, and thus can achieve the design of smaller memory complexity and lower power consumption. In the specific implementation, VLSI hardware can be used to achieve the multi-channel ORICA processor, real-time, lightweight and portable implementing separation and monitor of the brainwave signal, and can be used as in fast, lightweight and portable medical equipment applications.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A real-time multi-channel EEG signal processor based on an on-line recursive independent component analysis (ORICA), the real-time multi-channel EEG signal processor comprising:

an inverse square root matrix calculation unit for providing a computation of eigen value, eigen vector and inverse square root matrix;

a whitening unit coupled to the inverse square root matrix calculation unit for covariance computation of a sampling signal to generate a covariance matrix, wherein the covariance matrix generates a whitening matrix based on the computation of the inverse square root matrix calculation unit;

an ORICA calculation unit coupled to the inverse square root matrix calculation unit and the whitening unit for computing the sampling signal and the whitening matrix to obtain a post-whitening sampling signal, wherein an independent component analysis computation of the post-whitening sampling signal and a predetermined unmixing matrix is performed to obtain independent component data;

an ORICA training unit coupled to the inverse square root matrix calculation unit and the ORICA calculation unit for training the unmixing matrix according to the independent component data to obtain an inverse matrix of the unmixing matrix by the computation of the inverse square root matrix calculation unit, and computing the unmixing matrix and the inverse matrix of the unmixing matrix to generate a new unmixing matrix, wherein the new unmixing matrix is used for the ORICA calculation unit to perform a next independent component analysis computation of a next post-whitening sampling signal and the new unmixing matrix, so as to obtain next independent component data; and a memory unit coupled to the inverse square root matrix calculation unit, the whitening unit, the ORICA calculation unit and the ORICA training unit for storing the sampling signal, the whitening matrix and the unmixing matrix, the memory unit configured to temporarily store data generated by the inverse square root matrix calculation unit, the whitening unit, the ORICA calculation unit and the ORICA training unit so as to store the data in an ordered manner and enable memory sharing between the inverse square root matrix calculation unit, the whitening unit, the ORICA calculation unit and the ORICA training unit, wherein the ORICA training unit further comprises:

a nonlinearity module for computing the independent component data to obtain a non-linear transfer function;

a kurtosis estimation module for identifying the independent component data to be a super Gaussian signal or sub-Gaussian signal and generating a kurtosis value;

a multiplexer coupled to the nonlinearity module and the kurtosis estimation module for obtaining a nonlinear transfer function of independent component distribution data in accordance with the Gaussian signal or the sub-Gaussian signal and the kurtosis value;

a learning rate module for computing a learning rate determining convergence and steady state performance of the unmixing matrix during training; and a weight training module for implementing an iterative computation using the independent component data, the nonlinear transfer function of the independent component distribution data, the learning rate and the unmixing matrix, so as to generate the next unmixing matrix.

2. The real-time multi-channel EEG signal processor of claim 1, wherein the inverse square root matrix calculation unit comprises a singular value decomposition processor, a floating point square root module and a floating point divider.

3. The real-time multi-channel EEG signal processor of claim 2, wherein the singular value decomposition processor comprises two angle coordinate rotation digital computers and four vector coordinate rotation digital computers.

4. The real-time multi-channel EEG signal processor of claim 1, wherein the weight training module comprises eight multipliers and eight adders.

5. The real-time multi-channel EEG signal processor of claim 1, wherein the ORICA training unit further includes a learning rate module coupled to the weight training module for providing a plurality of learning rates, so as for the ORICA training unit to change a convergence rate of the unmixing matrix.

6. The real-time multi-channel EEG signal processor of claim 1, wherein the whitening unit comprises an average covariance module having a multiply-adder.

7. The real-time multi-channel EEG signal processor of claim 1, wherein the ORICA calculation unit comprises a scalar floating point multiply-adder.

8. The real-time multi-channel EEG signal processor of claim 1, wherein a sampling rate of the sampling signal is $1/128$ second.

* * * * *